US005380662A

United States Patent [19]

Robbins et al.

[11] Patent Number: 5,380,662

[45] Date of Patent: Jan. 10, 1995

[54] HYBRIDIZATION INCUBATOR WITH ROTISSERIE MECHANISM

[75] Inventors: Arthur J. Robbins; Michael D. Robbins, both of Mountain View, Calif.

[73] Assignee: Robbins Scientific Corporation, Calif.

[21] Appl. No.: 531,842

[22] Filed: Jun. 1, 1990

[51] Int. Cl.[6] .......... C12M 1/10

[52] U.S. Cl. .......... 435/312; 435/287; 435/316; 435/809; 422/99; 422/104; 366/214; 366/217

[58] Field of Search .......... 435/312, 316, 809, 287; 422/209, 104, 99; 366/198, 209, 213, 214, 217

[56] References Cited

U.S. PATENT DOCUMENTS

| | | | |
|---|---|---|---|
| 1,002,347 | 9/1911 | Wemer | 366/213 |
| 1,997,935 | 4/1935 | Johnson | 366/214 |
| 2,650,805 | 9/1953 | Schaefer | 366/214 |
| 3,090,604 | 5/1963 | Wheeler | 366/213 |
| 3,163,404 | 12/1964 | Kraft et al. | 366/214 |
| 3,232,247 | 2/1966 | Vaughan | 107/59 |
| 3,468,520 | 9/1969 | Duryea et al. | 259/39 |
| 3,695,162 | 10/1972 | Wing | 95/89 |
| 4,102,649 | 6/1978 | Sasaki | 23/259 |
| 4,461,578 | 7/1984 | Tiebout | 366/213 |
| 4,577,551 | 3/1986 | Bellanca | 99/348 |

FOREIGN PATENT DOCUMENTS 2202057 1/1971 Germany .

OTHER PUBLICATIONS

"The Controlled Environment Incubator," Technical Brochure of New Brunswick Scientific, N.J., 1966.

Fisher Scientific Catalog, 1988, pp. 630–631.

Bennahrnias, "An Alternative to the Water Bath/Plastic Bag Method for Hybridization of Southern and Northern Blots," American Biotechnology Laboratory, Sep. 1989.

*Primary Examiner*—James C. Housel
*Assistant Examiner*—Jan M. Ludlow
*Attorney, Agent, or Firm*—Michael J. Hughes

[57] ABSTRACT

A hybridization incubator assembly (10) is provided for incubation of samples contained in elongated sample bottles (16) and short sample bottles (60). The incubator (10) includes and oven body (18) which encloses a rotisserie assembly (14) adapted for carrying and agitating the sample bottles. The rotisserie assembly (14) includes a pair of bottle support wheels (43) mounted eccentrically on a drive shaft (40). The first wheel (44) and the second wheel (46) are mounted at different degrees of eccentricity and are axially separated on the drive shaft (40) by a distance slightly less than the length of the elongated bottles (16). Each support wheel (43) includes a plurality of grasping clamps (60) affixed about the rim portion (56) for holding the bottles (16), with each the grasping clamps (60) being paired with another on the opposing wheel (43) such that a bottle (16) may be supported by both wheels (43). The perimeter surface (58) of each wheel is beveled to facilitate agitation. The drive shaft (40) is caused to rotate by a drive motor (36) and a drive linkage (38) which cause the rotisserie assembly (14) to rotate about a rotational axis (41), thus transporting and agitating the samples within the oven cavity (28). The incubator (10) is primarily utilized for nucleotide hybridization procedures.

13 Claims, 3 Drawing Sheets

HYBRIDIZATION INCUBATOR WITH ROTISSERIE MECHANISM

TECHNICAL FIELD

The present invention relates to material handling apparatus and more specifically to devices for heating and agitating materials, and particularly to a hybridization incubator device having an agitating rotisserie mechanism.

BACKGROUND ART

A wide variety of applications involve circumstances where it is desirable to move an item while also exposing it to environmental factors such as heat, radiation, cold or the like. In many instances it is also desirable to agitate the item, if it has a fluid component, in order to insure maximum and uniform exposure of the contents of the item to the environmental condition.

One area in which this sort of technology is required is in automated cooking apparatus. In these circumstances it is often necessary to agitate or stir the contents of a cooking vessel while exposing it to heat. In many cases this is necessary to achieve uniform exposure. One example of a device adapted for this purpose is a fettuccine cooking apparatus described and shown in U.S. Pat. No. 4,577,551, issued to G. Bellanca. Another is found in the oven assembly of C. M. Vaughan, shown in U.S. Pat. No. 3,232,247. These two patents show methods utilized in the prior art to heat and agitate contents at the same time.

Another area of technology which requires agitation over a period of time is in the area of biological cultures. A device for agitating liquids, particularly those contained on sample trays, is shown in U.S. Pat. No. 4,102,649, issued to T. Sasaki. A further example of a method of agitating suspended cells in liquid is found in U.S. Pat. No. 3,468,520, issued to W. J. Duryea et. al. The object of each of these devices is to create an uniformity in the solution so that all of the contents will react at a similar rate.

In some instances the desirable goal is to utilize the liquid to uniformly wet a selected surface. An example of a U.S. Patent directed to this technology is U.S. Pat. No. 3,695,162, issued to R. Wing for a "Developing Machine For Photographic Film". In the Wing application it was desired to uniformly coat the photographic film with the developing chemicals so that an even rate of development was achieved.

The present invention is directed to a somewhat similar application in the fields of Biochemistry and Microbiology. Some of the processes utilized for study of gene structure, expressions and functions in all biological systems are the analysis of DNA and RNA species by hybridization to a radio isotope-Labeled Nucleotide Probe. This process is described in an article entitled "AN ALTERNATIVE TO THE WATERBATH/PLASTIC BAG METHOD FOR HYBRIDIZATION OF SOUTHERN AND NORTHERN BLOTS", by Sabrina Bennahmias, American Biotechnology Laboratory, September, 1989.

In the hybridization process the nucleic acids are separated by electrophoresis through a gel and are mobilized by capillary transfer to sheets of nitrocellulose or nylon membrane. The separate groupings of nucleic acid, referred to as "blots", are fixed on the membrane for later processing. One of the processes which is utilized in this procedure is to the wash the membranes in a buffer solution including a radioactive material referred to as a "probe". The radioactive probe selectively hybridizes the DNA and RNA nucleic acids which are complementary to the nucleotide sequence of the selected probe.

In order to achieve complete and uniform results it is necessary that the membrane containing the blot is uniformly exposed to the probe solution so as to achieve complete hybridization. It is also necessary that the hybridization take place within specific temperature ranges. The preferred temperatures for most of the hybridization processes presently used fall in the temperature range of 42° C. to 68° C. Reasonably precise temperature control and uniform temperature exposure are desirable in order to obtain consistent results.

Although, in the prior art, the hybridization was frequently performed in a shaker bath or "sandwich box", these methods occasionally had difficulties regarding spillage, material handling, volumes of probe utilized and waste disposal problems. Since the probe solution is radioactive in nature, any container or contents thereof which absorb any of the probe solution must be disposed of as radioactive waste. Therefore, it has become desirable to utilize non-absorbent containers, such as high quality borosilicate glass.

When glass bottles are utilized for the hybridization procedures the most efficient method of treating them is to utilize a temperature controlled oven mechanism with sample transport and agitation means within the oven. Although water baths and other heating mechanisms may be utilized, the oven has proved to be the most efficient and easily maintained. Various commercial temperature controlled ovens have been available in the marketplace for a lengthy period of time, and have been utilized for a variety of different processes. There have also been various methods utilized to rotationally move contents through an oven, such as the oven assembly of Vaughan.

However, none of the prior art structures has successfully solved all of the problems inherent in the hybridization process. Temperature uniformity, economy of manufacture and usage, and complete and uniform wetting with a minimum quantity of probe solution are all goals which have been approached, but not as closely as desired. Therefore, substantial room for improvement remains in the field.

DISCLOSURE OF THE INVENTION

Accordingly, it is an object of the present invention to provide an efficient drive mechanism for utilization within a hybridization incubator.

Another object of the present invention is to provide a drive mechanism which provides gentle but thorough agitation to the contents of sample bottles.

Yet another object of the present invention is to provide a rotisserie type bottle support and agitation mechanism which is easily and economically manufactured.

It is a further object of the present invention to provide agitation to hybridization bottles in a manner which minimizes the amount of probe solution required.

Briefly, a preferred embodiment of the present invention is a hybridization incubator assembly including a novel rotisserie-type agitation assembly. The agitation assembly includes a pair of opposed bottle support wheels mounted on a common drive shaft. Each of these support wheels is eccentrically mounted with respect to the rotational axis of the drive shaft with the angle of eccentricity of the second wheel being offset from that of the first wheel. In addition, the hubs of the wheels are beveled in such a manner that the bottles or other contents which are supported on either of the wheels are held at an angle with respect to the axis of rotation.

The primary utilization of the present invention is for the hybridization of nucleic acid blots on membranes which are contained within hybridization bottles. The invention is utilized either with elongated bottles which are supported on each end by grasping clamps on the first and second support wheels or with shorter bottles which are supported by only one clamp on one of the wheels. In the case of the elongated bottles the offset eccentricity of the two support wheels provides a constant and gentle sloshing type of axial agitation as the wheels rotate on the drive shaft. In the instance of the shorter bottles the axial agitation is provided by the beveled perimeter surfaces of the wheel rims which maintain the bottles at an angle with respect to the axis of rotation and further by the action of the eccentric mounting of the drive wheel. In all instances rotational agitation is provided to the fluids since the bottles are rigidly held in a single orientation with respect to the wheel rim while the fluids flow with gravity as the wheel rotates. The construction of the rotisserie-type agitation assembly has been found to yield extremely uniform coating and wetting results with a minimum amount of solution in the bottles.

Is therefore an advantage of the present invention that the agitation assembly provides consistent and effective agitation to the contents of the oven.

It is another advantage of the present invention that the agitation accomplishes uniform distribution of contents by a sloshing action requiring a minimum of content volume.

It is a further advantage of the present invention that the support wheels may be uniformly manufactured and the degree of eccentricity offset between the first and second support wheel may be determined at the time of assembly.

It is still another advantage of the present invention that a single uniform drive shaft may be utilized to deliver the rotational force in an eccentric manner, without requiring eccentric mounting of the drive shaft within the motor, thus reducing bearing wear.

It is still a further object of the present invention that it can be utilized, with similar agitation results, with either elongated bottles contacting both support wheels or with shorter bottles being supported on only one of the wheels.

It is yet another advantage of the present invention that the mechanisms for causing rotation and agitation are mechanically simple and thus require a minimum of maintenance.

These and other objects and advantages of the present invention will become clear to those skilled in the art in view of the description of the presently best known mode of carrying out the invention and the industrial applicability of the preferred embodiment as described herein and as illustrated in the several figures of the drawings.

BRIEF DESCRIPTIONS OF THE DRAWINGS

BEST MODE OF CARRYING OUT THE INVENTION

The primary component of the present invention is a rotisserie mechanism particularly adapted for use with a hybridization incubator. The primary intended use for the hybridization incubator including the novel rotisserie mechanism is for utilization in heating and rotating sample bottles in hybridization techniques. For these applications the contents of the sample bottles are agitated and constantly moved throughout the oven cavity so as to achieve uniform heating and relatively uniform agitation.

Figure 1:
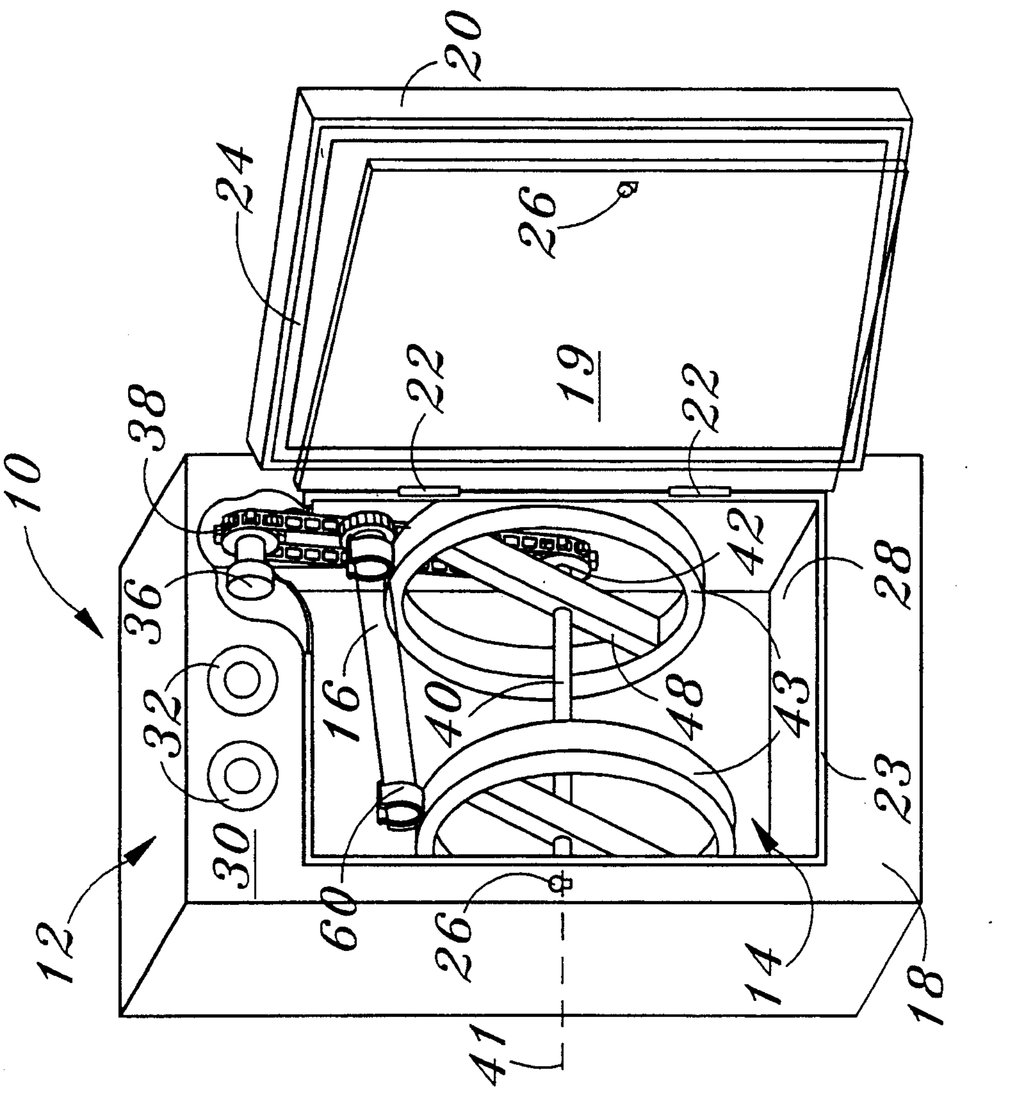
FIG. 1 is a perspective view of a hybridization incubator according to the present invention.

Referring now to FIG. 1, a hybridization incubator including the rotisserie of the preferred embodiment of the present invention is illustrated in a perspective manner and is designated by the general reference character 10. It may be seen that the hybridization incubator 10 includes an overall oven assembly 12 and a rotisserie assembly 14 which is contained within the oven assembly 12. The rotisserie assembly 14 is shown in this illustration as supporting only a single sample bottle 16, although it is adapted for supporting ten elongated bottles 16 of the type shown. The oven assembly 12 is primarily conventional in nature and includes the same components as previously available laboratory ovens. As shown in FIG. 1, the oven assembly 12 includes an oven body 18, a partially transparent inner door 19 and a heavier, opaque outer door 20. Both doors 19 and 20 are attached at one edge to the oven body 18 by conventional hinge structures 22.

The dual door structure is useful to researchers utilizing the incubator 10 in that this feature allows the user to observe the rotisserie assembly 14 and the sample bottles 16 without disturbing the interior environment. A first sealing gasket 23 is attached to the oven body 18 such that the interior surface of the inner door 19 forms a seal with the first gasket 23. A second sealing gasket 24 is placed on the interior surface of the outer door 20 such that the inner door 19 nests inside of the second gasket 24 when both doors are either open or closed. A latching mechanism 26 is provided on the inner door 19 to allow the user to mechanically latch and unlatch the inner door 19 when desired. The second sealing gasket 24 is magnetized in the same manner as that found on conventional refrigerator doors such that the magnetic attraction between the magnetic gasket 24 and the metallic oven body 18 holds the outer door 20 in a closed position unless pulled open.

An interior cavity 28 is defined by the oven body 18 and the inner door 19. The interior cavity 28 is environmentally isolated from the surroundings by the insulated walls of the oven body 18 and the doors 19 and 20 and the associated gaskets 23 and 24. The inner door 19 is transparent to allow observation of the interior cavity 28 while air flow is inhibited. However, since the inner door 29 is not overly effective as a thermal insulator, and since constant observation is not ordinarily required, the heavier, thermally insulating outer door 20 is closed in most circumstances to avoid heat loss.

A control panel 30 is provided on the oven body 18 at a position which is accessible whether the doors 19 and 20 are open or closed. The control panel 30 includes a variety of specific user-accessible control 32 which adjust such factors as the oven temperature, as well as additional controls such as on/off switches.

The interior cavity 28 is the spatial volume in which the desired operations of the hybridization incubator 10 take place. The rotisserie assembly 14 is contained within the interior cavity 28 and is attached to the oven body 18 by attachments to the structure situated within the oven body 18 but exterior to a pair of opposed side walls 34 of the interior cavity 28.

As shown in FIG. 1, the rotisserie assembly 14 is a rotating mechanism with the rotational power being supplied by a drive motor 36 contained within the upper oven body 18 as shown in the partially cut away side wall 34. The drive motor 36 delivers rotational force to a drive linkage 38 in the form of a sprocket and chain assembly. Any form of rotational force transfer system would be effective but the preferred incubator 10 utilizes a sprocket attached to the motor 36, a chain extending downward within the wall of the oven body 18 and a second sprocket opposite about the middle of the interior cavity 28. The drive linkage 38, when turned by the drive motor 36, rotates a drive shaft 40 about a rotational axis 41 which is horizontal with respect to the ordinary orientation of the hybridization incubator 10. The drive shaft 40 is supported on a pair of shaft bearings/support structures 42 which are situated at the points where the drive shaft 40 intersects the side walls 34.

Figure 2:
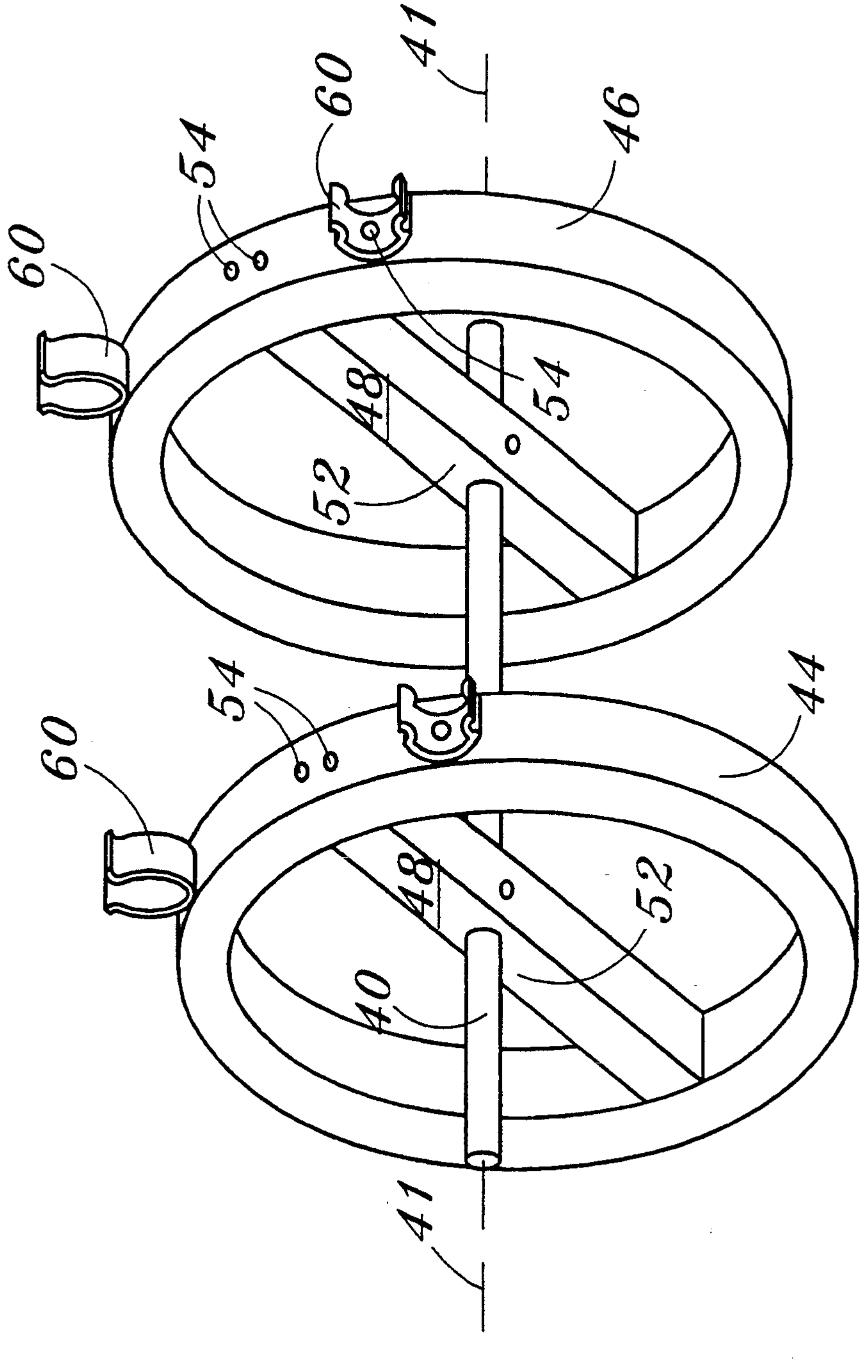
FIG. 2 is a perspective view of the rotisserie-type drive/agitation assembly of the present invention, shown separately.

The rotisserie assembly 14 is illustrated in a perspective view in FIG. 2 and is shown as being separated from the oven assembly 12. The detailed construction of the rotisserie assembly 14 is best understood from a consideration of all of FIGS. 1 through 4, but the primary illustration is FIG. 2. In this illustration it maybe seen that the rotisserie assembly 14 includes, in addition to the drive shaft 40, a pair of sample bottle support wheels 43. These are referred to as a first support wheel 44 and second support wheel 46. The support wheels 43 are adapted to support the sample bottles 16 and to carry the sample bottles 16 along a rotational path within the interior cavity 28.

Each of the support wheels 43 is attached to the drive shaft 40 by way of a mounting bar 48. The manner in which the mounting bar 48 is attached to the support wheel 44 and the drive shaft 40 is best illustrated in the side view of FIG. 3. In this illustration it maybe seen that the mounting bar 48 includes a shaft aperture 50 extending therethrough such that the support wheel 43 may be attached to the drive shaft 40.

The placement of the shaft aperture 50 is critical to the operation of the inventive rotisserie assembly 14 in that it provides for axial agitation of the contents of the sample bottle 16 when the drive shaft 40 is rotated. The reason that the agitation occurs may be seen in FIG. 3. If a pair of orthogonal diameters are imagined with the respect to the circular support wheel 43, these orthogonal diameters will intersect at an origin point 52 for the support wheel 43. The origin point 52 represents the center of the support wheel 43 from a geometrical standpoint. In order to achieve uniform rotation of the support wheel 43 the axis of rotation 41 would pass through the origin point 52. However, in the present invention, the shaft aperture 50 is selected to be offset from the origin point 52 such that the rotational axis 41, which corresponds to the drive shaft 40, intersects the mounting bar 48 and the support wheel structure at a point offset from the origin point 52. This offset creates a degree of eccentricity for the support wheels 43 such that when the drive shaft 40 is rotated the support wheel 43 will have an eccentric rotation with respect to its own geometric center of balance.

As is shown in FIG. 2, the location of the origin point 52 with respect to the rotational axis 41 is different on the first support wheel 44 than on the second support wheel 46. Thus the angle of the eccentricity, defined as the angle of rotation of the line segment including the origin point 52 and the shaft aperture 50 about the rotational axis 41 compared to an arbitrarily selected position, such as vertically upward, is different for the two wheels 43. This enhances the agitation action upon the sample bottle 16 since the ends of the sample bottle 16 are constantly at different and varying offsets from the axis of rotation 41.

In the preferred embodiment 10, the eccentricity offsets of the first wheel 44 and the second wheel 46 are 180° opposite. This is accomplished for manufacturing convenience. With this configuration, all of the mounting bars 48 may be manufactured to the same specifications and oppositely mounted with respect to the support wheels 44 and 46. This configuration also provides the esthetically balanced effect of having the mounting bars 48 arrayed in a coplanar fashion. Of course, the degree and angle of relative eccentricity offset between the wheels 44 and 46 may be altered by changing the location of the shaft aperture 50 on the mounting bar or by abandoning the coplanar alignment of the mounting bars 48. However, it is important that the alignment be selected such that bottle holding elements on each wheel 43 are aligned.

Figure 3:
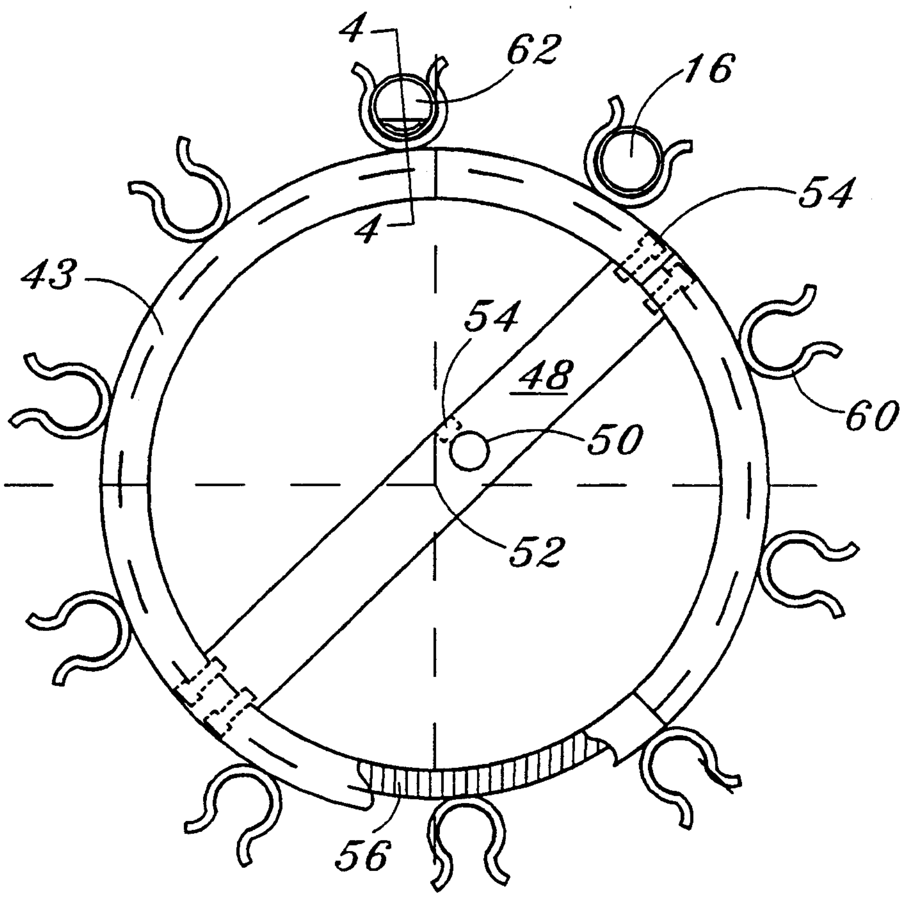
FIG. 3 is a side elevational view of one of the support wheels.

It may also be seen in FIG. 3 that a portion of the rotisserie assembly 14 is held together by a plurality of securing fasteners 54. The securing fasteners 54 are utilized to secure the outer portion of the support wheels 43 to the mounting bar 48 and also to secure the mounting bar 48 to the drive shaft 40. The securing fasteners 54 selected maybe metal screws, bolts, rivets or the like. In order to facilitate maintenance and repair it is preferred to utilize metal screws which may be easily removed and replaced when necessary.

It maybe also seen in FIG. 3 that the rim portion 56 of the support wheel 43 includes a circumferential perimeter surface 58 which is beveled or slanted with respect to both the axis of rotation and to a perpendicular axis passing through the origin point 52. This maybe best seen from the vantage point of FIG. 4, which shows a portion of the rim 56 of the wheel 43 in a cross sectional view. This view also illustrates the manner in which a sample bottle 16 is supported on the support wheel 43.

As is shown in FIG. 3, the preferred embodiment of the support wheel 43 includes ten equally spaced grasping clamps 60, each of which is adapted to receive a standard diameter sample bottle 16. Each grasping clamp 60 is paired with a corresponding clamp 60 on the opposite wheel 43 but, in the preferred embodiment 10, is rotationally offset from the paired opposing clamp 60 to provide additional sloshing. The grasping clamps 60 are typically flexible stainless steel or anodized aluminum elements generally shaped like a lyre and adapted to expand sufficiently to allow easy insertion and removal of the sample bottles 16. The grasping clamps 60 are also sufficiently rigid such that the sample bottles 16 do not become accidentally detached. Since the borosilicate glass of the sample bottle 16 is a relatively heavy material it is necessary that each grasping clamp 60 be constructed of strong material and have a substantial degree of resiliency.

Figure 4:
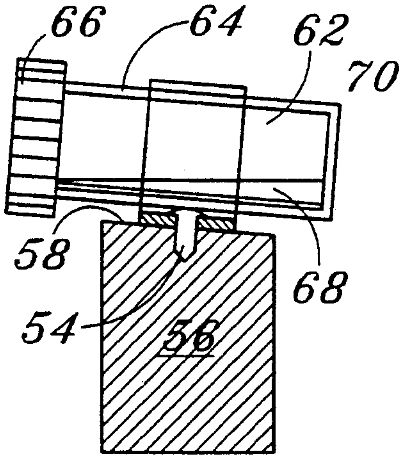
FIG. 4 is a cross-sectional view, taken along line 4—4 of FIG. 3.

The illustration of FIG. 4 shows an alternate short sample bottle 62 held within one of the grasping clamps 60. Whereas the sample bottle 16 illustrated in FIG. 1 is supported on both the first support wheel 44 and the second support wheel 46, the short bottle 62 is supported on only one support wheel 43. If short bottles 62 are utilized the rotisserie assembly 14 of the preferred embodiment will support twenty (20) short bottles 62 rather than ten (10) elongated bottles 16.

It maybe seen that both types of the sample bottles 16 and 62 (although only the short bottle 62 is illustrated in FIG. 4), include a tube portion 64 and a screw-type cap 66 which seals the tube portion 64. In the primary utilization of the present invention, the tube portion 64 encloses one or more membranes 68 which are adapted to be thoroughly wetted by a probe solution 70. It is the sloshing and agitation of the probe solution 70 with respect to the membrane 68 that is the primary object of the structure of the rotisserie assembly 14.

Since the preferred embodiment of the hybridization incubator 10 is adapted for utilization with nucleic acid hybridization techniques it is desirable that all of the components which may possibly come into contact with the radioactive probe solution 70 will be nonretentive materials that are easily cleaned and retain none of the radioactivity. Therefore, the components which exist within the interior cavity 28 are preferably constructed of anodized aluminum or polished stainless steel, both of which may be easily cleaned.

Precise dimensions and ratios of dimensions of the components of the preferred embodiment of the hybridization incubator 10 are a matter of choice and are dependent upon the particular utilization intended. However, for the presently preferred embodiment 10, which is adapted to be utilized with sample bottles 16 having a diameter of 42 mm and a length of 300 mm (and short bottle 62 having the same diameter but a length of 150 mm), the following dimensions apply. The interior cavity 28 of the oven portion 12 is selected to be cubical in nature and have a wall length of 33 cm (13 inch). The drive shaft 40 has a diameter of 1.26 cm (0.50 inch) and a length of 35.3 cm (14 inch). Each of the support wheels 43 is selected to have a diameter of 17.6 cm (7.0 inch) from interior facing outside to opposing interior facing outside edge and a diameter of 17.4 cm (6.9 inch) from opposing exterior facing edges. This represent a beveling in the amount of 0.2 cm (0.1 inch) from interior edge to exterior edge, as illustrated in FIG. 4. The interior diameter of the rim portion 56 is 15.1 cm (6.0 inch).

One key area of modification which may be utilized to increase or reduce the amount of agitation is to alter the eccentricity of the support wheels with respect to the axis of rotation 41. As discussed above, this alteration may be accomplished either by altering the magnitude of offset for one or both of the wheels 43 or it may be accomplished by altering the degree or direction of offset of eccentricity between the two wheels 44 and 46 or the rotational offset of the pairs clamps 60. If the second option is selected the agitation will be altered only with respect to the full length sample bottles 16 and not with respect to the short bottles 62. If the actual magnitude of eccentricity for each of the wheels 44 and 46 is changed then the degree of agitation for the short bottles 62 will also be altered. Similarly, the agitation of the contents of the short bottles 62, particularly, will be further altered by changing the angle of inclination of the perimeter surface 58. The greater the angling of the perimeter surface 58 with respect to the axis of rotation 41, the greater the sloshing that will occur as the support wheels 43 are rotated. It is noted that the angle of the perimeter surface 58 does not have any significant impact on the agitation of the large sample bottles 16 because the angle imparted to the sample bottle 16 by the angling of the perimeter surface 58 and the associated grasping clamp 60 is overcome by the necessity of attaching the sample bottle 16 to another grasping clamp 60 on the opposing support wheel 43. The clamps 60 allow enough freedom of motion to permit this type of attachment.

Various other modifications and alterations of the assembly may be made without departing from the invention. Those skilled in the art will readily recognize alternate embodiments and utilizations. Accordingly, the above disclosure is not to be construed as limiting and the appended claims are to be interpreted as encompassing the entire spirit and scope of the invention.

INDUSTRIAL APPLICABILITY

The hybridization incubator 10 according to the present invention is primarily adapted to be utilized with nucleic acid hybridization techniques as described in the *Bennahmias* article referred to above. For the sake of example, the typical utilization is described below:

The sample bottles 16 or 62 will be prepared independently according to standard laboratory techniques prior utilization of the invention. In order to show the flexibility of usage it will presumed that five (5) of the longer standard sample bottles 16 have been prepared and ten (10) of the short bottles 62 are prepared.

As the bottles are being prepared the hybridization incubator 10 will be preheated to a selected temperature. For a typical hybridization application the selected temperature will be 55° C. and the controls 32 will be set in such a manner that this uniform temperature is achieved in the interior cavity 28 before insertion of the sample bottles 16.

The door latch mechanism 26 is electrically tied to the drive motor 36 in such a manner that when the inner door 19 is open the drive motor 36 will cut out and the powered rotation of the rotisserie assembly 14 will stop. Thus, when the user opens the inner door 19 the rotisserie 14 will stop and the user will be able to place bottles in the grasping clamps 60 which are most easily accessible. The support wheels 43 may then be advanced by utilizing a motor jog switch 32 on the control panel 30 to turn the wheels 43 to the next position and the next bottles maybe placed within the grasping clamps 60, either one long bottle 16 or two short bottles 62, until all of the grasping clamps 60 are filled. Of course, the rotisserie assembly 14 works equally well if less than all of the positions are filled.

When the inner door 19 is subsequently closed and latched the drive motor 36 will then be again activated and the rotisserie assembly 14 will turn within the interior cavity 28, thus uniformly heating and agitating the sample bottles 16 and 62. The outer door 20 will typically also be closed for maximum heat retention, although it may be opened occasionally to permit visual inspection. The temperature may be adjusted by the controls 32.

Because of the offset eccentricity between the first support wheel 44 and the second support wheel 46 and due to the rotational offset of the clamps 60, the various ends of the longer sample bottle 16 will be at different orientations with respect to the axis of rotation 41, at different position within the interior cavity 28, during rotation. This creates a sloshing action along the direction of the axis of rotation 41 as well as the rotational sloshing which occurs during rotation since the bottles 16 themselves are rigidly held within the clamps 60. This sloshing motion in three dimensions assures maximal wetting of the membrane 68 with the convenience and economy of utilizing a minimum amount of probe solution 70.

With respect to the short bottle 62 a similar result is achieved because of the eccentricity of the support wheel 43 which imparts some sloshing along the axis of rotation 41 and also because of the angling of the perimeter surface 58 which results in corresponding angling of the short bottles 62, as shown in FIG. 4. Again, maximal wetting of the membrane 68 with a minimum amount of probe solution 70 is accomplished. When the hybridization incubation or other process has run for the desired length of time it is merely necessary to open the outer door 20 and the inner door 19 (stopping the drive mechanism) and remove the bottles in the inverse of the process used to place them within the incubator 10. The incubator 10 then is available to be utilized again either at the same setting or at different settings.

All of the above aspects and advantages make the present invention of extreme value in laboratory usages. The ease of use, the limitation of necessary probe solution 70 and the avoidance of spillage and contamination are all of significant importance to professionals engaged in hybridization and similar processes. Accordingly, it is expected that the present invention will enjoy immediate, long term, and widespread industrial applicability and commercial utility.

We claim:

1. A hybridization incubator assembly, comprising:

an oven subassembly for providing an enclosed volume within which controlled temperature conditions may be maintained; and a rotisserie subassembly, at least a substantial portion of which is enclosed within the oven subassembly, for supporting and transporting a plurality of sample holding components on a continuous pathway within said enclosed volume, wherein the rotisserie subassembly is characterized by having a pair of generally circular support wheels mounted on a single rotatable horizontally arrayed drive shaft, with each said support wheel mounted perpendicularly and eccentrically on said drive shaft such that said sample holding components are supported on the rim portions of said support wheels and the contents of said sample holding components are agitated as said drive shaft is rotated.

2. The incubator assembly of claim 1 wherein said sample holding components are a plurality of elongated bottles adapted to enclose contents which are at least partially fluid.

3. The incubator assembly of claim 2 wherein said plurality of elongated bottles are supported on each end thereof by a corresponding plurality of grasping clamps respectively mounted on said support wheels.

4. The incubator assembly of claim 1 wherein said drive shaft is caused to rotate in a controlled manner about a rotational axis by drive shaft motor means.

5. The incubator assembly of claim 2 wherein said support wheels are axially separated on said drive shaft by a distance less than the length of said elongated bottles, such that said bottles may be simultaneously supported by both of said support wheels.

6. The incubator assembly of claim 1 wherein each said support wheel includes a mounting bar extending diametrically between opposing positions on said rim portions, said mounting bar including a shaft aperture therethrough for receiving said drive shaft, the position of the shaft aperture being offset from the origin point of said support wheel.

7. The incubator assembly of claim 6 wherein the angle of offset of the position of said shaft aperture from said origin point is different for said two different support wheels.

8. A rotisserie assembly for carrying fluid-containing receptacles along a generally circular path about an axis of rotation, comprising:

a drive shaft extending along the axis of rotation so as to rotate thereabout;

a first generally circular wheel member perpendicularly and eccentrically mounted on the drive shaft, the first wheel member including a rim portion having a plurality of receptacle support components attached to the peripheral surface thereof and a mounting portion for attaching said rim portion to the drive shaft;

a second wheel member, similar in construction to the first wheel, eccentrically mounted on the drive shaft at a position axially separated from the first wheel member; and rotational motive means for rotating the drive shaft.

9. The rotisserie assembly of claim 8 wherein at least some of the fluid-containing receptacles are in the form of elongated bottles; and the magnitude of the axial separation between the first wheel member and the second wheel member is less than the length of said elongated bottles, such that a single one of said bottle members may be supported on a pair of receptacle support components, with one of said pair being situated on each wheel member.

10. The rotisserie assembly of claim 9 wherein the angle of said eccentric mounting of the second wheel member on the drive shaft, with respect to said axis of rotation is offset with respect to the angle of said eccentric mounting of the first wheel member on the drive shaft.

11. The rotisserie assembly of claim 8 wherein said mounting portion is in the form of a mounting bar extending diametrically across said rim portion, said mounting bar including a shaft receiving aperture formed therethrough for receiving the drive shaft, said shaft receiving aperture being positioned such that the axis of rotation does not pass through the origin point of the wheel member.

12. The rotisserie assembly of claim 8 wherein said rim member is axially beveled on the circumferential surface thereof, said receptacle support components being mounted on said circumferential surface such that receptacles supported solely thereby are supported such that the major axes of the receptacles are offset from parallel to the axis of rotation.

13. The rotisserie assembly of claim 8 wherein the rotational motive means includes an electrical motor and a rotational force transfer linkage for translating the force from said motor to the drive shaft.

* * * * *

UNITED STATES PATENT AND TRADEMARK OFFICE

CERTIFICATE OF CORRECTION

PATENT NO. : 5,380,662

DATED : Jan. 10, 1995

INVENTOR(S) : Robbins, Arthur J.; Robbins, Michael D.

It is certified that error appears in the above-indentified patent and that said Letters Patent is hereby corrected as shown below:

Title page, item [56] References Cited: "Bennahrnias" should read --Bennahmias--

Title page, item [57] Abstract (3rd line of Abstract): "sample bottles (60)" should read --sample bottles (62)--

UNITED STATES PATENT AND TRADEMARK OFFICE

CERTIFICATE OF CORRECTION

PATENT NO. : 5,380,662

DATED : Jan. 10, 1995

INVENTOR(S) : Robbins, Arthur J.; Robbins, Michael D.

It is certified that error appears in the above-indentified patent and that said Letters Patent is hereby corrected as shown below:

| Column | Line | Correction |
|---|---|---|
| 1 | 66 | "acid, referred to as "blots", are fixed on the membrane" should read --acid are fixed on the membrane and are referred to as "blots."-- |
| 1 | 67 | Delete "for later processing." |
| 1 | 68 | "the wash" should read --wash-- |
| 2 | 7 | Delete "containing the blot" |
| 3 | 31 | "Is" should read --It is-- |
| 8 | 32 | Insert --to-- after "prior" |
| 8 | 33 | Insert --be-- after "will" |
| 9 | 4 | "position" should read --positions-- |

Signed and Sealed this

Twenty-seventh Day of June, 1995

*Attest:*

Bruce Lehman

BRUCE LEHMAN

*Attesting Officer* *Commissioner of Patents and Trademarks*